United States Patent
Hirst et al.

(10) Patent No.: US 12,254,981 B2
(45) Date of Patent: *Mar. 18, 2025

(54) METHOD AND COMPUTER-READABLE RECORDING MEDIUM FOR USING A SELF-DESCRIBING MODULE FOR UPDATING DATA IN A MEDICAL MONITORING DEVICE

(71) Applicant: Drägerwerk AG & Co. KGaA, Lübeck (DE)

(72) Inventors: Michael D. Hirst, Webster, MA (US); Joshua Abell, Beverly, MA (US); Geoffrey Waite, Topsfield, MA (US); Stefan Schlichting, Lubeck (DE); Alexander Loose, Reinfeld (DE); Hannes Molsen, Lubeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/638,854

(22) Filed: Apr. 18, 2024

(65) Prior Publication Data

US 2024/0347194 A1    Oct. 17, 2024

Related U.S. Application Data

(63) Continuation of application No. 17/045,687, filed as application No. PCT/EP2019/058853 on Apr. 8, 2019, now Pat. No. 11,990,237.

(Continued)

(51) Int. Cl.
*G16H 40/67* (2018.01)
*G06F 8/65* (2018.01)
(Continued)

(52) U.S. Cl.
CPC ............. *G16H 40/67* (2018.01); *G06F 8/65* (2013.01); *G16H 10/60* (2018.01); *G16H 40/40* (2018.01)

(58) Field of Classification Search
CPC ........ G16H 40/67; G16H 10/60; G16H 40/40; G16H 40/63; G16H 15/00; G06F 8/65
See application file for complete search history.

(56) References Cited

U.S. PATENT DOCUMENTS

2012/0226768 A1 * 9/2012 Gaines ................ G16H 40/67
709/217

FOREIGN PATENT DOCUMENTS

WO    WO-2016100811 A1 *  6/2016  ....... G06F 17/30867

OTHER PUBLICATIONS

Schrader, Andreas, Darren Carlson, and Peter Rothenpieler. "Smartassist-wireless sensor networks for unobtrusive health monitoring." Proceedings of the 5th BMI Workshop on Behaviour Monitoring and Interpretation, CEUR Workshop Proceedings, Karlsruhe, Germany, Sep. vol. 21. 2010 (Year: 2010).*

* cited by examiner

*Primary Examiner* — Linh Giang Le
(74) *Attorney, Agent, or Firm* — Nolte Lackenbach Siegel (57) ABSTRACT

A method and computer-readable recording media using a self-describing module for updating data in a medical monitoring device. The self-describing module includes a meta-data block (MDB) that includes at least identification (ID) data and corresponding configuration data. The medical monitoring device includes a plurality of sub-systems. Associating ID data from the MDB with ID data of the plurality of sub-systems of the medical monitoring device, and then (Continued)

updating configuration data of at least one sub-system with the configuration data in the MDB based on the result of the association.

22 Claims, 9 Drawing Sheets

Related U.S. Application Data (60) Provisional application No. 62/654,218, filed on Apr. 6, 2018.

(51) Int. Cl.
*G16H 10/60* (2018.01)
*G16H 40/40* (2018.01)

METHOD AND COMPUTER-READABLE RECORDING MEDIUM FOR USING A SELF-DESCRIBING MODULE FOR UPDATING DATA IN A MEDICAL MONITORING DEVICE

CROSS-REFERENCE TO RELATED APPLICATION(S)

This application is a continuation of U.S. application Ser. No. 17/045,687, filed Oct. 6, 2020, which is a national phase entry of PCT International Application No. PCT/EP2019/058853, filed Apr. 8, 2019, which claims the benefit of U.S. Provisional Application No. 62/654,218, filed Apr. 6, 2018, the entire contents of which are hereby fully incorporated by reference.

BACKGROUND

The subject matter of the present disclosure relates generally to updating data in medical monitoring devices.

Conventional models for interfacing patient front-ends to medical devices create software on the medical device, which is specifically designed for handling data from the front-end. However, these conventional models also introduce issues that need to be addressed. One issue is that it is difficult to add a new parameter to the front-end without also updating software on the medical device because the medical device must have the capability to process the new parameter. Additionally, since both the parameters and software in the medical devices are updated together, they are also tested and released as a system. Moreover, new revisions of the software may not be compatible with previously released medical devices at customer locations.

Thus, it would be advantageous and an improvement over the relevant technology to provide a method for a self-describing module to efficiently and easily update data in medical monitoring devices.

SUMMARY

Embodiments described in the present disclosure provide methods for implementing a self-describing module for updating data in a medical monitoring device. The methods include transmitting a metadata block (MDB) from the self-describing module to the medical monitoring device using a communication interface, the MDB including at least identification (ID) data and corresponding configuration data; optionally storing the MDB in memory of the medical monitoring device as an instance of MDB data; associating the ID data from the MDB with ID data of a plurality of sub-systems of the medical monitoring device; and updating configuration data of at least one sub-system of the medical monitoring device with the configuration data in the MDB based on a result of the association between ID data from the MDB and the ID data of the plurality of sub-systems.

Embodiments described in the present disclosure provide a non-transitory computer-readable recording medium in the self-describing module for updating data in the medical monitoring device. The non-transitory computer-readable recording medium stores one or more programs which when executed by a processor performs the steps of the method described above.

BRIEF DESCRIPTION OF THE DRAWINGS

In the drawings, like reference numbers generally indicate identical, functionally similar, and/or structurally similar elements.

DETAILED DESCRIPTION

Figure 1:
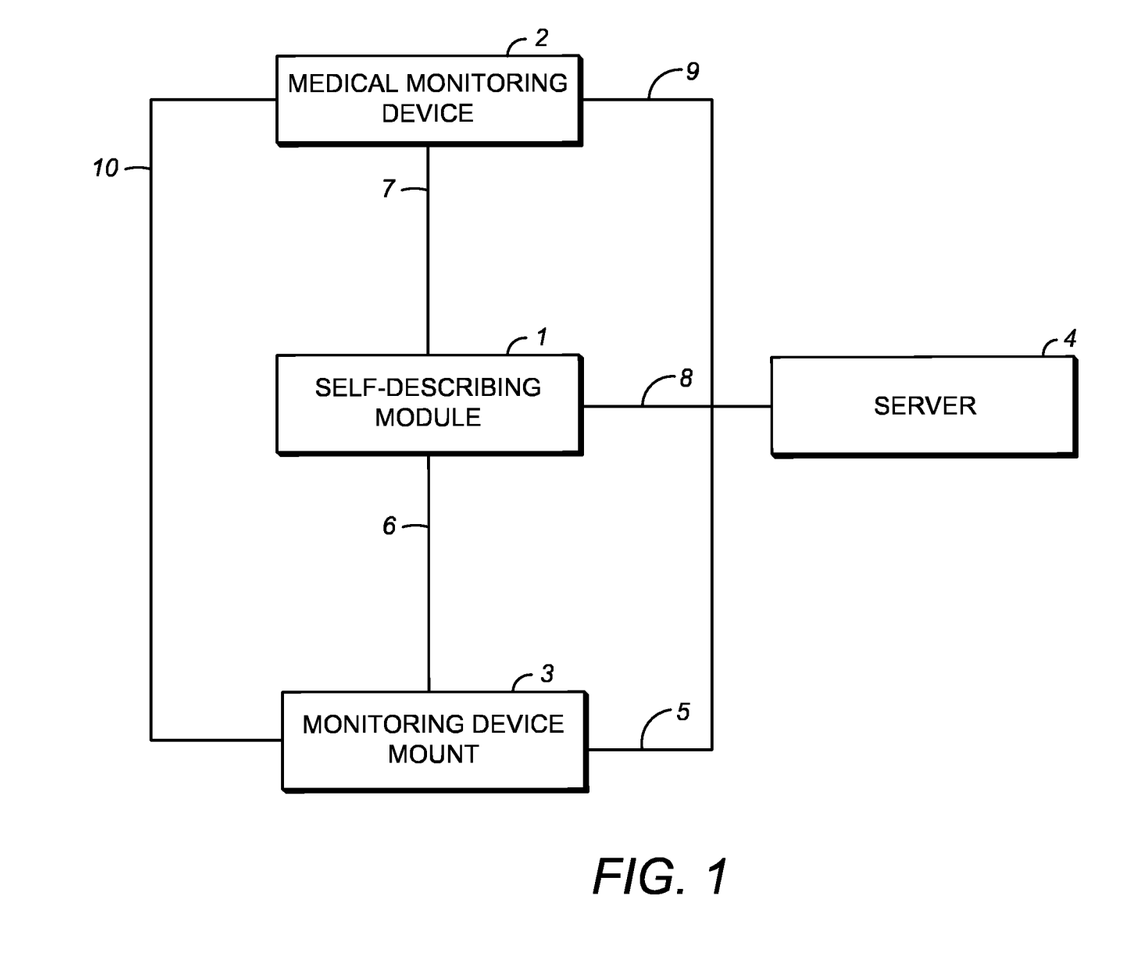
FIG. 1 is a schematic diagram of a system for using a self-describing module for updating data in a medical monitoring device according to an embodiment of the present disclosure.

FIG. 1 is a schematic diagram of a system for using a self-describing module for updating data in a medical monitoring device. As shown in FIG. 1, the system includes a self-describing module 1, a medical monitoring device 2, an optional monitoring device mount 3, and one or more servers 4.

An explanation of exemplary internal components of the self-describing module 1, medical monitoring device 2, optional monitoring device mount 3, and one or more servers 4 shown in FIG. 1 will be provided in the discussion of FIGS. 6 through 9. However, in general, it is contemplated by the present disclosure that the self-describing module 1, medical monitoring device 2, optional monitoring device mount 3, and one or more servers 4 include electronic components or electronic computing devices operable to receive, transmit, process, store, and/or manage data and information associated with the system, which encompasses any suitable processing device adapted to perform computing tasks consistent with the execution of computer-readable instructions stored in a memory or a computer-readable recording medium.

Further, any, all, or some of the computing devices in the self-describing module 1, medical monitoring device 2, optional monitoring device mount 3, and one or more servers 4 may be adapted to execute any operating system, including Linux, UNIX, Windows Server, etc., as well as virtual machines adapted to virtualize execution of a particular operating system, including customized and proprietary operating systems. The self-describing module 1, medical monitoring device 2, optional monitoring device mount 3, and one or more servers 4 are further equipped with components to facilitate communication with other computing devices over the one or more connections 5, 6, 7, 8, 9, 10. The connections 5, 6, 7, 8, 9, 10 include connections to local and wide area networks, wireless and wired networks, public and private networks, and any other communication network enabling communication in the system. Additionally, it is also contemplated by the present disclosure that the connections 5, 6, 7, 8, 9, 10 can include, but are not limited to, a universal serial bus (USB) connection, a serial peripheral interface (SPI) connection, an Ethernet connection, coaxial connection, a wireless connection, a High-Definition Multimedia Interface (HDMI) connection, wireless connection, or other serial transport connection, and any combinations thereof.

In FIG. 1, the self-describing module 1, medical monitoring device 2, optional monitoring device mount 3, and one or more servers 4 are shown connected through the network connections 5, 6, 7, 8, 9, 10. Each of these components can include one or more computing devices depending on a desired configuration. The self-describing module 1, medical monitoring device 2, optional monitoring device mount 3, and one or more servers 4 can include one or more programmable data processors and memories or memory locations for storing the software components. In the self-describing module 1, the memory includes a metadata block (MDB) 14 that will be further discussed below. The one or more memories in the self-describing module 1 include, but are not limited to, random access memory (RAM), dynamic random access memory (DRAM), read only memory (ROM), logic blocks of a field programmable gate array (FPGA), erasable programmable read only memory (EPROM), and electrically erasable programmable ROM (EEPROM).

In certain embodiments, the self-describing module 1 is a patient monitoring module, or interfacing patient front-end module, configured to acquire and process data generated by at least one physiological sensor configured to monitor a physiological parameter of a patient. The process data generated by sensors such as ECG electrodes, SPO2 sensor, blood pressure cuffs, apnea detection sensors, respirators, and the like which measure physiological parameters such as blood pressure, heart related information, pulse oximetry, respiration information, and the like. The MDB 14 includes settings needed by a physiological algorithm of the self-describing module 1. These include patient categories such as neonate, pediatric, adult, etc. The MDB 14 includes, for example, the self-describing module 1 settings needed by the physiological algorithm such as user changeable filter settings. User changeable filter settings can include values for limits for alarm settings and the like. Having these values in the self-describing module 1 allows for updates and the like to occur through the self-describing module 1 (e.g. updates such as version revisions).

In order to leverage new functionality, the self-describing module 1 can provide flexibility in several ways. Customers can adopt the latest algorithms, features and software updates for parameter measurement devices without waiting for releases of a new version from the medical monitoring device 2. Users can configure the number and type of parameter measurement devices to meet varied and changing clinical needs. A service approach can be more unified than currently provided, with remote access to versions, logs, self-tests, settings, history, and measurements via the internet to all parameter measurement devices.

The MDB 14 can include data or information for delivering the self-describing configuration of the self-describing module 1 to a consumer such as the medical monitoring device 2. The MDB 14 can inform the medical monitoring device 2 as to what data is produced as well as additional properties for various sub-systems and display elements within the medical monitoring device 2. The MDB 14 can include a plurality of plug-ins, which are software interfaces for allowing communication of the data for the respective subsystems. Each plug-in can engage with the medical monitoring device 2. Each plug-in can be implemented for each consumer of the self-describing module 1 data. Additionally, the MDB 14 can include information on how to use the data produced by the self-describing module 1, how data is formatted, how often the data is updated, how the data should be displayed, and how the data should be labelled.

The MDB 14 can include device identification (ID) data such as data types, update rate, alarm limits, settings and other characteristics. Reporting of physiological measurements, for example, and settings including waveforms can be included in the MDB 14 in the form of metrics. Additionally, the MDB 14 supports at least one or more of the following: alerts, remote control of the self-describing module 1, service relevant data retrieval including device metadata, logs, software updates, and localized text strings with a localized database. The localized text strings include metrics, alerts, and remote control elements supported by the self-describing module 1.

The MDB 14 can also include a subset of a medical device communication standard, which describes and communicates a state of the self-described module 1. The nomenclature and coding system from the standard, such as IEEE 11073-10207 (Standard for Domain Information and Service Model for Service-Oriented Point-of-Care Medical Device Communication), can provide status of the state of the self-describing module 1. The MDB 14 can include a medical data information base (MDIB), which is a collection of data objects that are provided by a particular medical device including descriptive and state information.

In certain embodiments, the medical monitoring device 2 is a patient monitor that is used to monitor various physiological parameters for a patient. The medical monitoring device 2 can be portable and travel with the patient in order to provide continuous monitoring during care. The medical monitoring device 2 connects via wired and/or wireless interfaces to one or more sensors such as ECG electrodes, SPO2 sensor, blood pressure cuffs, apnea detection sensors, respirators, and the like which measure the physiological parameters such as blood pressure, heart related information, pulse oximetry, respiration information, and the like associated with the patient. Additional types of information can be conveyed through the medical monitoring device 2. The medical monitoring device 2 can process and/or display analog data derived from the patient The medical monitoring device 2 includes a plurality of sub-systems 12. The plurality of sub-systems 12 can include sub-systems for at least one graphical user interface (GUI), for trends, alarms, reports, network, and the like. In this or another embodiment, the medical monitoring device 2 can include at least one metadata plugin interface (MPI). Each sub-system of the plurality of sub-systems 12 can include one of the MPIs and each MPI can have a version associated with it. The MPIs engages with the MDB 14 so that plug-ins of the MDB 14 can associate with the MPI of the a sub-system 12. Each of the MPIs can be updated with a new interface while leaving interfaces that are already in place unchanged. The MDB 14 of the self-describing module 1 can include a plurality of plug-ins that connect to the MPIs. The medical monitoring device 2 can connect to at least one patient sensor 11, such as ECG electrodes, SPO2 sensor, blood pressure cuffs, apnea detection sensors, respirators, and the like, that provides patient data to the medical monitoring device 2.

The MDB 14 can provide a consumer or user of a medical monitoring device 2 with information about what data is being provided and the properties for various sub-systems as well as enable the display of elements within the medical monitoring device 2. The MDB 14 includes identification (ID) data and corresponding configuration data for the various sub-systems 12 in the medical monitoring device 2.

The monitoring device mount 3 can be an optional component. The monitoring device mount 3 can provide physical support, a power source, and a conduit to one or more computer networks. In certain embodiments when the medical monitoring device 2 is not used in transport of a patient, the monitoring device mount 3 can be connected. It is contemplated by the present disclosure that, in certain embodiments, the medical monitoring device 2 can connect (e.g., connection 6) to the monitoring device mount 3. In these embodiments, the self-describing module 1 connects to the monitoring device mount 3 and communication from the self-describing module 1 to the medical monitoring device 2 is established through the monitoring device mount 3 (e.g., connection 10). The embodiments below describe in more detail exemplary communications from and to the self-describing module 1 and the medical monitoring device 2 through the monitoring device mount 3.

Figure 2:
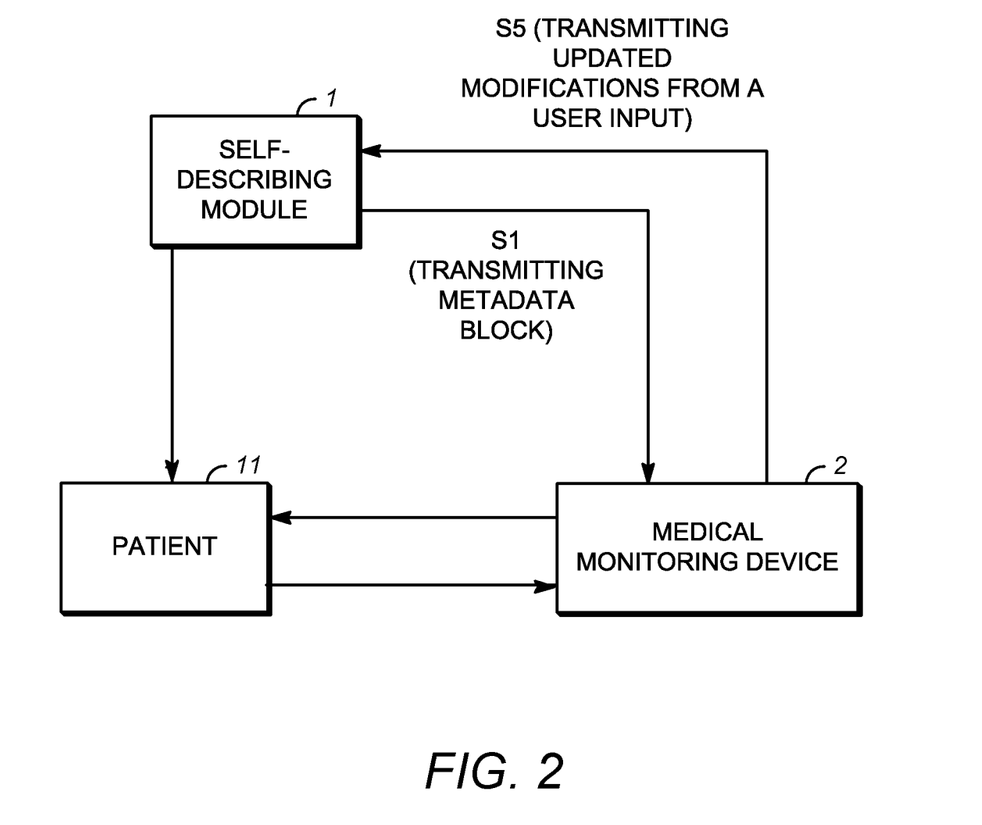
FIG. 2 illustrates a method for using a self-describing module for updating data in a medical monitoring device using the system of FIG. 1 according to an embodiment of the present disclosure.
Figure 3:
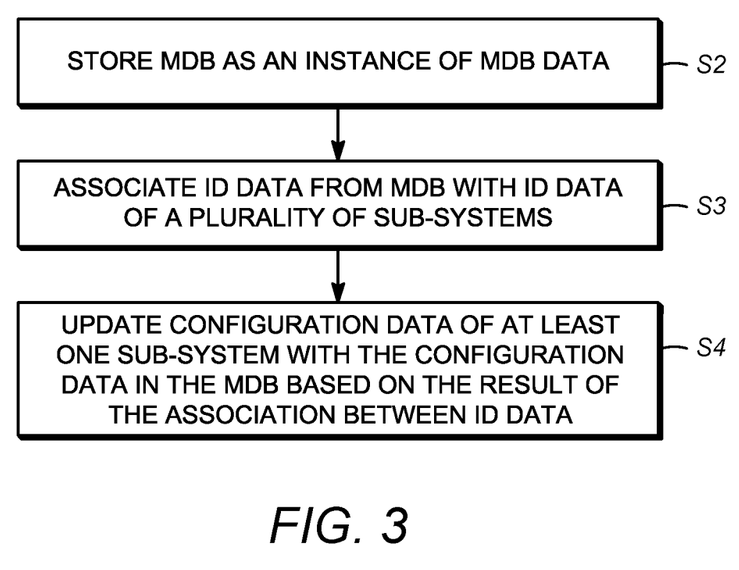
FIG. 3 illustrates a method performed by the medical monitoring device for using a self-describing module for updating data in a medical monitoring device using the system in FIG. 1 according to an embodiment of the present disclosure.

FIG. 2 illustrates a method for using a self-describing module 1 for updating data in a medical monitoring device 2. In step S1, the self-describing module 1 transmits the MDB 14 to the medical monitoring device 2. The information provided in the MDB 14 includes the description of metrics that the self-describing module 1 supports. The process performed by the medical monitoring device 2 after receiving the MDB 14 is described with reference to FIG. 3 and steps S2-S4. In step S2, the medical monitoring device 2 stores the MDB data as an instance of MDB data 13 in the memory of the medical monitoring device 2, which is described in more detail in FIG. 4. The instance of MDB data 13 then is used to associate the ID data from the MDB 14 with the ID data of the plurality of sub-systems 12 in step S3. When the ID data is unknown to the medical monitoring device 2, the ID data can be ignored. In step S4, updating of configuration data is performed of at least one sub-system of the plurality of sub-systems 12 with the configuration data in the instance of MDB 13 based on the result of the association between the two ID data. At runtime, the state of the metrics change in the MDB 14 and are received by the medical monitoring device 2. In certain embodiments, step S2 is not necessary, and the medical monitoring device 2 transmits the information from the MDB 14 over the network through one or more of the network connections 5, 6, 7, 8, 9, 10 instead of storing the MDB data as an instance in the memory of the medical monitoring device 2. Then in the following step S3, MDB data 14 then is used to associate the ID data from the MDB 14 with the ID data of the plurality of sub-systems 12 in step S3.

In certain situations, a user may desire to adjust the data that is provided by the MDB 14 and self-describing module 1. An example of a change made by a user would be the limits for alarms to be adjusted a for a particular department. The medical monitoring device 2 includes a user interface for facilitating communication between the medical monitoring device 2 and the user. The user interface allows for a user to input changes to the data. Returning to FIG. 2, a user can transmit updated sub-system data modifications made in the medical monitoring device 2 to the self-describing module 1 using the user interface, as shown in step S5. The updated sub-system modifications can be, for example, transmitted from the medical monitoring device 2 to the self-describing module 1 in reference to the physiological sensors monitoring a patient.

Figure 4:
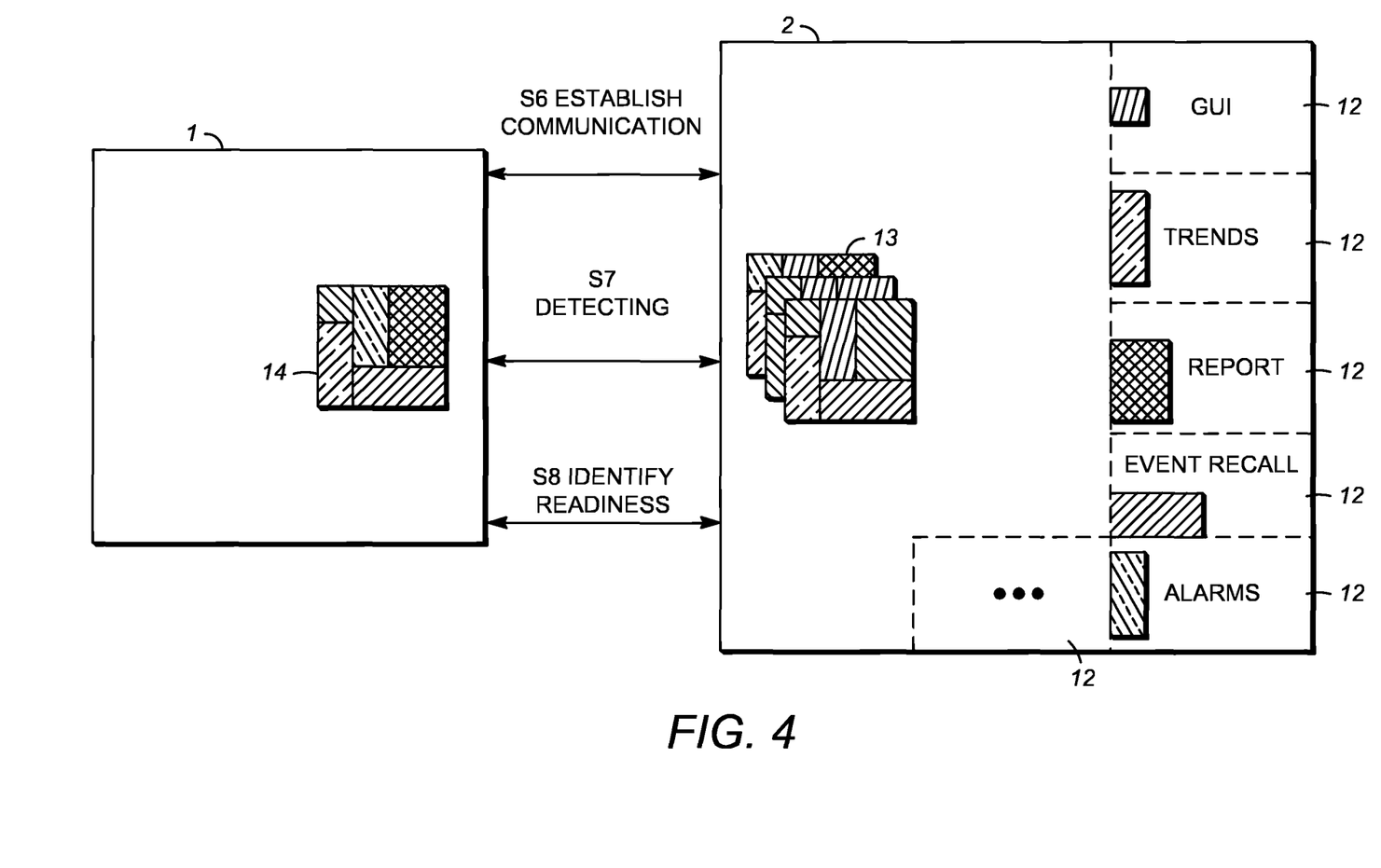
FIG. 4 illustrates a method for implementing the self-describing module for updating data in a medical monitoring device using the system of FIG. 1 according to an embodiment of the present disclosure.
Figure 5:
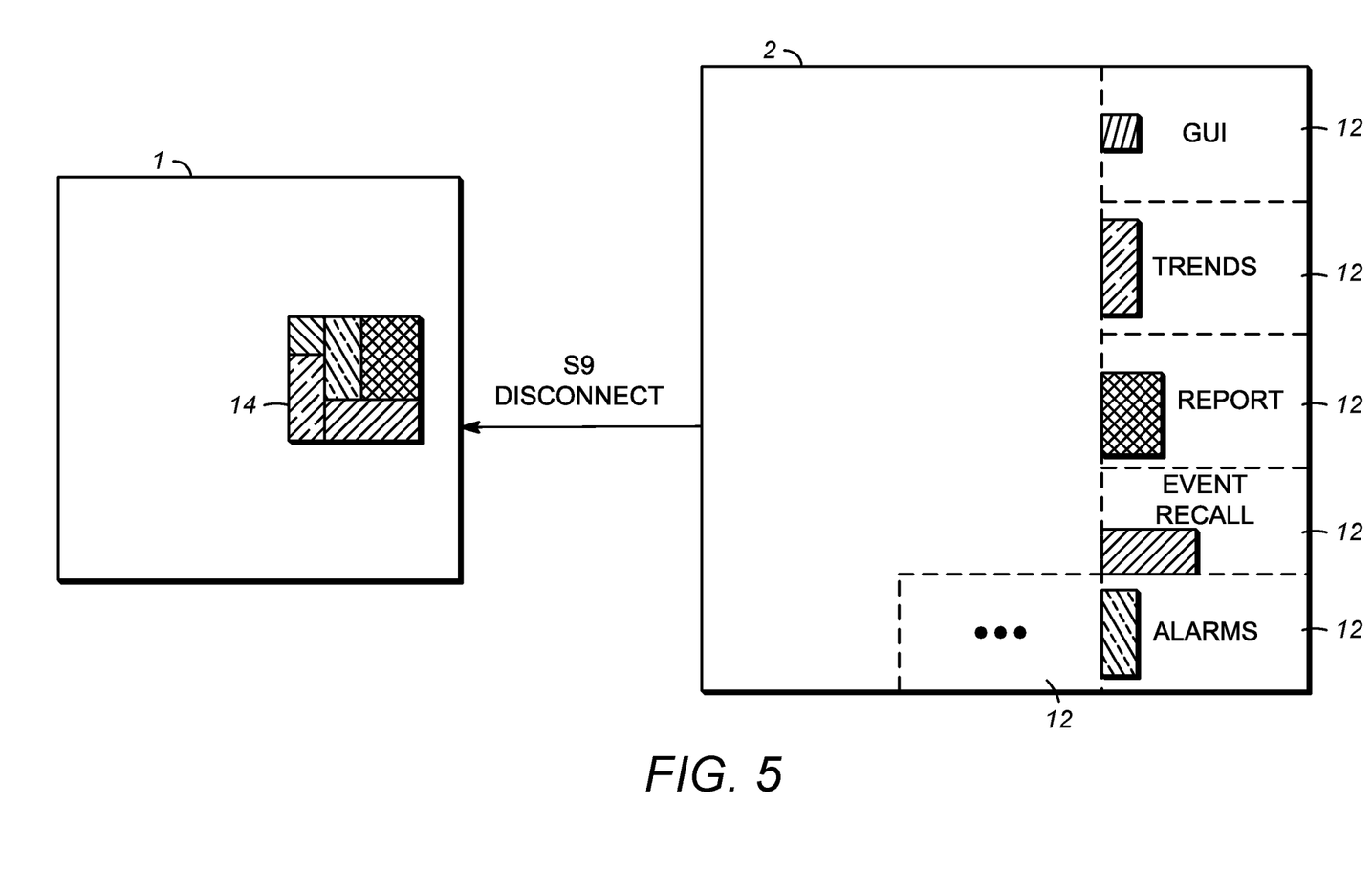
FIG. 5 illustrates a method for updating data in a medical monitoring device using a self-describing module according to an embodiment of the present disclosure.

FIGS. 4 and 5 illustrate communication between the self-describing module 1 and the medical monitoring device 2. In FIG. 4, step S6 through step S8 are shown as potential initial steps in the communication process. Communication can first be established in step S6 between the self-describing module 1 and the medical monitoring device 2 through a connection (e.g., connection 7). Examples of the connection includes a USB port, a SPI port, an Ethernet port, or other similar connection. Once connected, the medical monitoring device 2 can then detect the self-describing module 1 in step S7. For example, the self-describing module 1 can have a generic driver associated with the self-describing module 1 and the driver can enable the medical monitoring device 2 to detect the self-describing module 1.

In step S8, each sub-system 12 of the plurality of sub-systems 12 in the medical monitoring device 2 can identify a readiness within each of the sub-systems 12 to process data. The identification of readiness can occur based on an announcement transmitted from each sub-system 12 of the medical monitoring device 2. The announcement can be a ready signal that is transmitted to the self-describing module 1 from the medical monitoring device 2 once all the sub-systems of the plurality of sub-systems 12 are initiated and ready for communications.

FIG. 5 illustrates when the self-describing module 1 is disconnected from the medical monitoring device 2. Once there is a disconnection between the self-describing module 1 and the medical monitoring device 2, as in step S9, the instance of the MDB 13 that was stored in the medical monitoring device 2, is removed from the memory of the medical monitoring device 2 in embodiments that store the instance of the MDB 13. The removal of the instance of the MDB 13 when there is a disconnection is a way to ensure that the medical monitoring device 2 is always operated with a correct, up-to-date version of the MDB 14. The MDB 14 is transmitted by the self-describing module 1 to the medical monitoring device 2 each time the self-describing module 1 is connected. Once a self-describing module 1 is reconnected to the medical monitoring device 2, the method as described herewithin is repeated.

The self-describing module 1 may be removed from the medical monitoring device 2 for various reasons. Examples of reasons for disconnecting include, but is not limited to, updating the self-describing module 1 with new versions, new parameters, new algorithms, features, or software. Updates to the medical monitoring device 2 can also be handled through updates to the self-describing module 1.

When new parameters are added to the self-describing module 1 within the MDB 14, an update is required in the plurality of sub-systems in the medical monitoring device 2. Once a self-describing module 1 is reconnected, or connected for the first time to the medical monitoring device 2, all parameters that are present in the MDB 14 are provided in the MDB instance 13 that is stored in the medical monitoring device 2. Therefore, there is no need to replace or remove the medical monitoring device 2. In certain embodiments, the medical monitoring device 2 can be placed into a service mode that is protected while the uploads of new versions of the MDB 14 and MPIs are taking place. Additionally, in certain embodiments with no storage of the MDB instance 13, all parameters that are present in the MDB 14 are provided, as transmitted, through the medical monitoring device 2.

The ID data from each plug-in can include a namespace identifier for association with the MPI of the particular sub-system 12 supporting a particular namespace. When a namespace is unknown to the medical monitoring device 2, the namespace can be ignored.

The self-describing module 1 can communicate with a user through the medical monitoring device 2 and user interface of the medical monitoring device 2. Additionally, as mentioned above, the self-describing module 1 communicates with the medical monitoring device 2 in various ways such as, without limitation, how data is formatted, how often the data is updated, how the data should be displayed, and/or how the data should be labelled. A common set of connectors can be used between the self-describing module 1 and the medical monitoring device 2 that can reduce or eliminate the need for different variations on each monitor. Further, there can be a timely introduction of the latest clinical measurement technology through updates of the self-describing module 1, that the medical monitoring device 2 receives through the method described herewithin.

Figure 6:
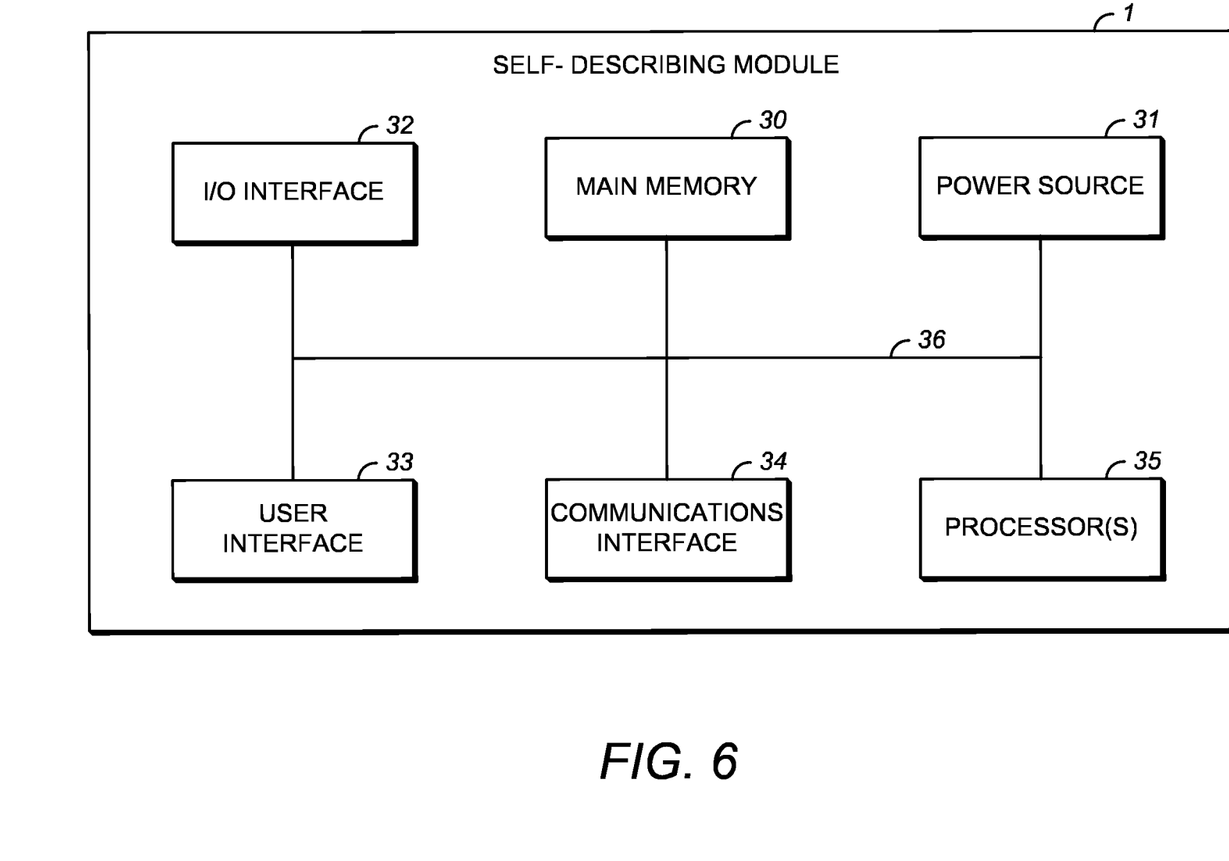
FIG. 6 is a schematic diagram of an exemplary self-describing module according to an embodiment of the present disclosure.

FIG. 6 is a schematic diagram of an exemplary self-describing module according to an embodiment of the present disclosure. It is contemplated by the present disclosure that the self-describing module 1 include electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium.

As shown in FIG. 6, the exemplary self-describing module 1 includes one or memories or memory locations including a main memory 30 as well as an I/O interface 32, a user interface 33, a communications interface 34, one or more processors 35, and an optional power source 31. The main memory 30 can be a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy.

The main memory 30 can be used to store any type of instructions associated with algorithms, processes, or operations for controlling the general functions of the self-describing module 1 including the operations of the MDB as well as any operating system such as Linux, UNIX, Windows Server, or other customized and proprietary operating systems.

The optional power source 31 can be used to power the various components of the self-describing module 1. The power source 31 can be self-contained, such as a battery pack, and/or the power source 31 can include an interface to be powered through an electrical outlet (either directly or by way of the medical monitoring device 2 and/or the monitoring device mount 3). In certain embodiments, the self-describing module 1 can only be powered and render information when secured or otherwise connected to one or more of the medical monitoring device 2 and the monitoring device mount 3.

The I/O interface 32 can be an interface for enabling the transfer of information between self-describing module 1 and external devices such as the medical monitoring device 2 or the optional monitoring device mount 3 that need special communication links for interfacing with the one or more processors 35. The I/O interface 32 can be implemented to accommodate various connections to the self-describing module 1 that include, but is not limited to, a universal serial bus (USB) connection, a serial peripheral interface (SPI) connection, an Ethernet connection, coaxial connection, a wireless connection, a High-Definition Multimedia Interface (HDMI) connection or other serial transport connection or other known connection in the art for connecting to external devices.

The user interface 33 is implemented for allowing communication between a user and the self-describing module 1. The user interface 33 includes, but is not limited to, a liquid crystal display (LCD), cathode ray tube (CRT), thin film transistor (TFT), light-emitting diode (LED), high definition (HD) or other similar display device with touch screen capabilities. Other kinds of input devices can be used to provide for interaction with a user as well. For example, feedback provided to the user can be any form of sensory feedback (e.g. visual feedback, auditory feedback by way of a speaker, or tactile feedback), and input from the user can be received in any form, including acoustic, speech, or tactile input. Input devices and a microphone can be coupled to and convey information via the internal bus 36 by way of an input device interface. A speaker can be coupled to and receive information via the internal bus 36 by way of a speaker interface. The self-describing module 1 can omit or one or more of the display, display interface, input device, microphone, speaker, input device interface, and speaker interface. The communications interface 34 is a software and/or hardware interface implemented to establish a connection between the self-describing module 1 and the server 4 in the system described in FIG. 1. It is contemplated by the present disclosure that the communications interface 34 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), and wireless local area networks (WLANs), system area networks (SANs), and other similar networks.

The one or more processors 35 are used for controlling the general operations of the self-describing module 1. Each one or the one or more processors 35 can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of the self-describing module 1. Communication between the components of the self-describing module 1 (e.g., 30-35) are established using an internal bus 36.

Figure 7:
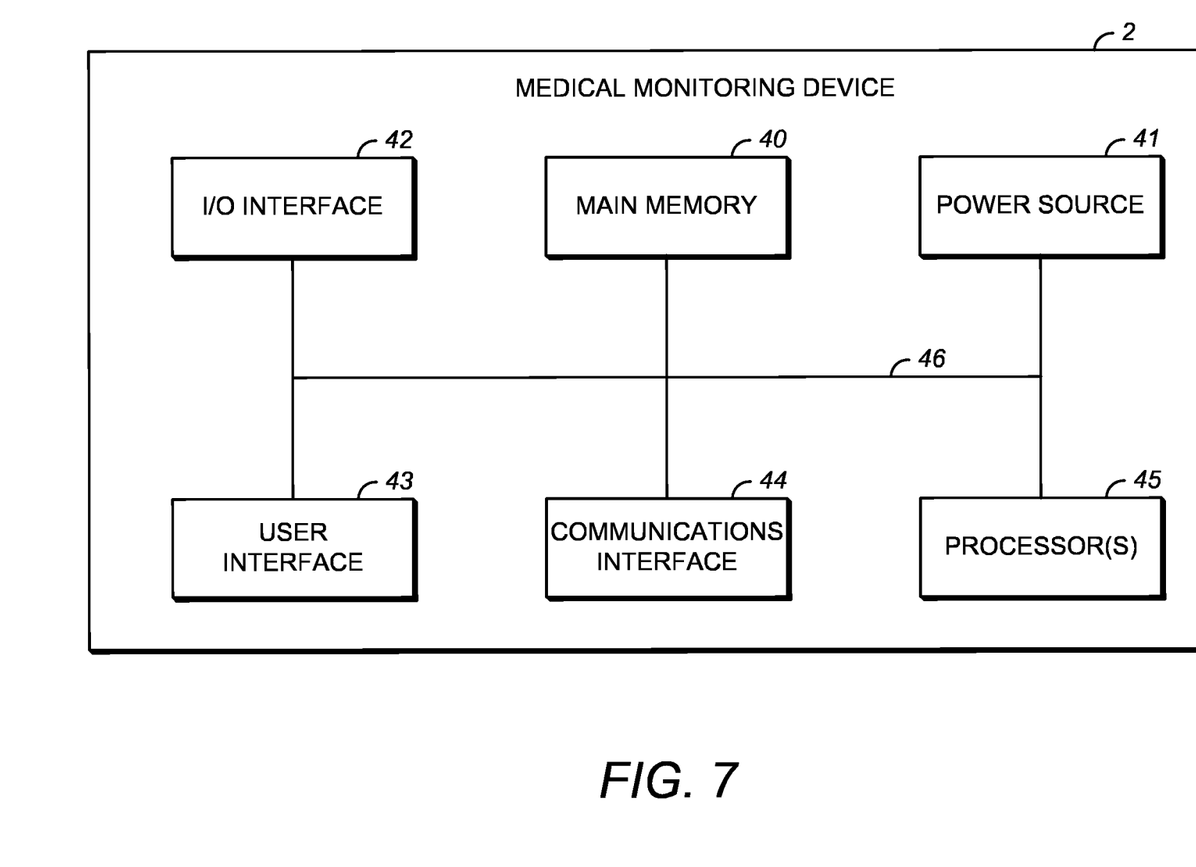
FIG. 7 is a schematic diagram of an exemplary medical monitoring device according to an embodiment of the present disclosure.

FIG. 7 is a schematic diagram of an exemplary medical monitoring device according to an embodiment of the present disclosure. It is contemplated by the present disclosure that the medical monitoring device 2 include electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium.

As shown in FIG. 7, the exemplary medical monitoring device 2 includes one or memories or memory locations including a main memory 40 as well as an I/O interface 42, a user interface 43, a communications interface 44, one or more processors 45, and an optional power source 41. The main memory 40 can be a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy.

The main memory 40 can be used to store any type of instructions associated with algorithms, processes, or operations for controlling the general functions of the medical monitoring device 2 including the operations of the plurality of sub-systems 12, the storage of MDB 13 as well as any operating system such as Linux, UNIX, Windows Server, or other customized and proprietary operating systems.

The optional power source 41 can be used to power the various components of the medical monitoring device 2. The power source 41 can be self-contained, such as a battery pack, and/or the power source 41 can include an interface to be powered through an electrical outlet (either directly or by way of the monitoring device mount 3).

The I/O interface 42 can be an interface for enabling the transfer of information between medical monitoring device 2 and external devices such as sensors for the monitoring of physiological parameters for a patient or medical devices, or the self-describing module 1 or the optional monitoring device mount 3 that need special communication links for interfacing with the one or more processors 45. The I/O interface 42 can be implemented to accommodate various wired and/or wireless connections to the medical monitoring device 2 that include, but is not limited to, ECG electrodes, SPO2 sensor, blood pressure cuffs, apnea detection sensors, respirators, and the like, or a universal serial bus (USB) connection, parallel connection, a serial connection, coaxial connection, a wireless connection, a High-Definition Multimedia Interface (HDMI) connection, SPI connection, other serial transport connection, or other known connection in the art for connecting to external devices.

The user interface 43 is implemented for allowing communication between a user and the medical monitoring device 2. The user interface 43 includes, but is not limited to, a liquid crystal display (LCD), cathode ray tube (CRT), thin film transistor (TFT), light-emitting diode (LED), high definition (HD) or other similar display device with touch screen capabilities. Other kinds of input devices can be used to provide for interaction with a user as well. For example, feedback provided to the user can be any form of sensory feedback (e.g. visual feedback, auditory feedback by way of a speaker, or tactile feedback), and input from the user can be received in any form, including acoustic, speech, or tactile input. Input devices and a microphone can be coupled to and convey information via the internal bus 46 by way of an input device interface. A speaker can be coupled to and receive information via the internal bus 46 by way of a speaker interface. The medical monitoring device 2 can omit or one or more of the display, display interface, input device, microphone, speaker, input device interface, and speaker interface. The communications interface 44 is a software and/or hardware interface implemented to establish a connection between the medical monitoring device 2 and the server 4 either directly or indirectly through the monitoring device mount 3 in the system described in FIG. 1. It is contemplated by the present disclosure that the communications interface 44 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), and wireless local area networks (WLANs), system area networks (SANs), and other similar networks.

The one or more processors 45 are used for controlling the general operations of the medical monitoring device 2. Each one or the one or more processors 45 can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of the medical monitoring device 2. Communication between the components of the medical monitoring device 2 (e.g., 40-45) are established using an internal bus 46.

Figure 8:
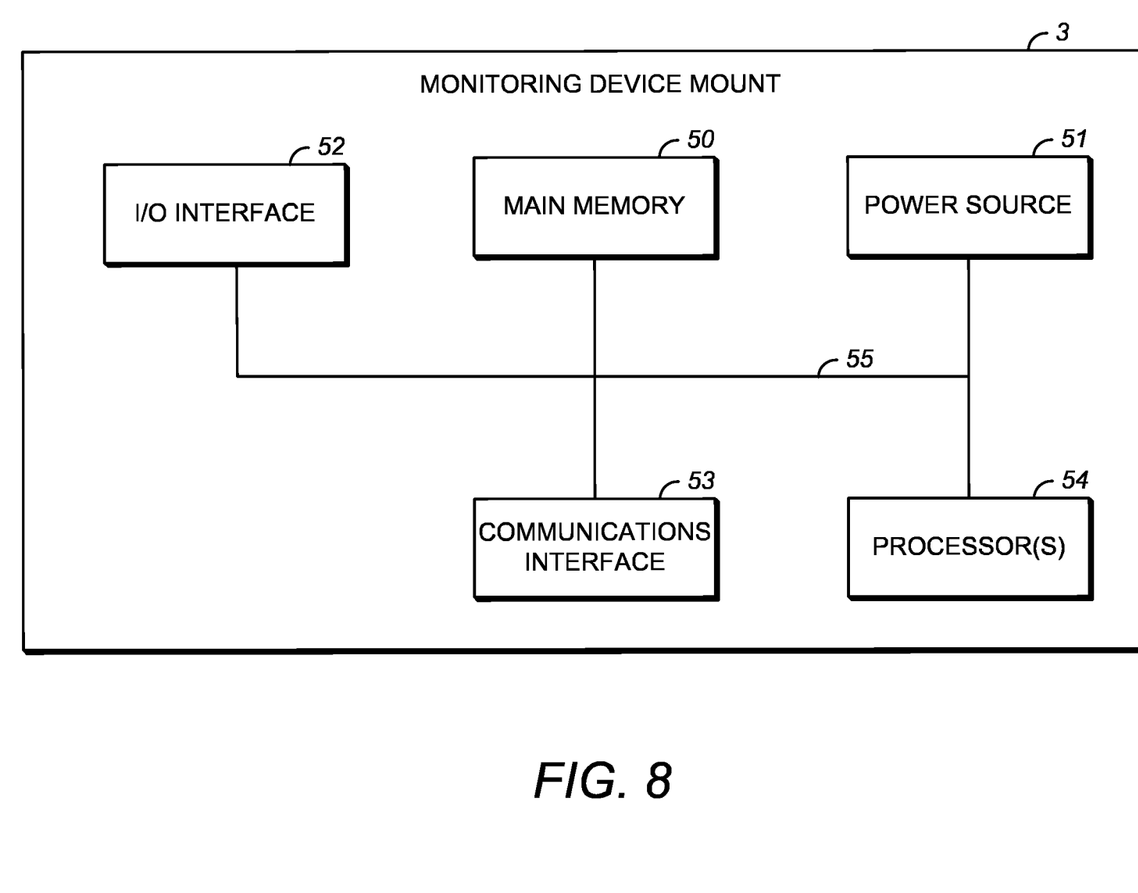
FIG. 8 is a schematic diagram of an exemplary monitoring device mount according to an embodiment of the present disclosure.

FIG. 8 is a schematic diagram of an exemplary monitoring device mount according to an embodiment of the present disclosure. It is contemplated by the present disclosure that the monitoring device mount 3 include electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium.

As shown in FIG. 8, the exemplary monitoring device mount 3 optionally includes one or memories or memory locations including a main memory 50 as well as an I/O interface 52, a communications interface 53, optionally one or more processors 54, and an optional power source 51. The main memory 50 can be a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy.

The main memory 50 can be used to store any type of instructions associated with algorithms, processes, or operations for controlling the general functions of the monitoring device mount 3 including the operations of the monitoring device mount 3 as well as any operating system such as Linux, UNIX, Windows Server, or other customized and proprietary operating systems.

The optional power source 51 can be used to power the various components of the monitoring device mount 3 and/or the medical monitoring device 2 and the self-describing module 1. The power source 51 can be self-contained, such as a battery pack, and/or the power source 51 can include an interface to be powered through an electrical outlet.

The I/O interface 52 can be an interface for enabling the transfer of information between monitoring device mount 3 and external devices such as the medical monitoring device 2 or the self-describing module 1 that need special communication links for interfacing with the one or more processors 54. The I/O interface 52 can be implemented to accommodate various connections to the monitoring device mount 3 that include, but is not limited to, a universal serial bus (USB) connection, parallel connection, a serial connection, coaxial connection, a wireless connection, a High-Definition Multimedia Interface (HDMI) connection, SPI connection, other serial transport connection, or other known connection in the art for connecting to external devices.

The communications interface 53 is a software and/or hardware interface implemented to establish a connection between the monitoring device mount 3 and the server 4 in the system described in FIG. 1. It is contemplated by the present disclosure that the communications interface 53 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), and wireless local area networks (WLANs), system area networks (SANs), and other similar networks.

The optional one or more processors 54 are used for controlling the general operations of the monitoring device mount 3. Each one or the one or more processors 54 can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of the monitoring device mount 3. Communication between the components of the self-describing module 1 (e.g., 50-54) are established using an internal bus 55.

Figure 9:
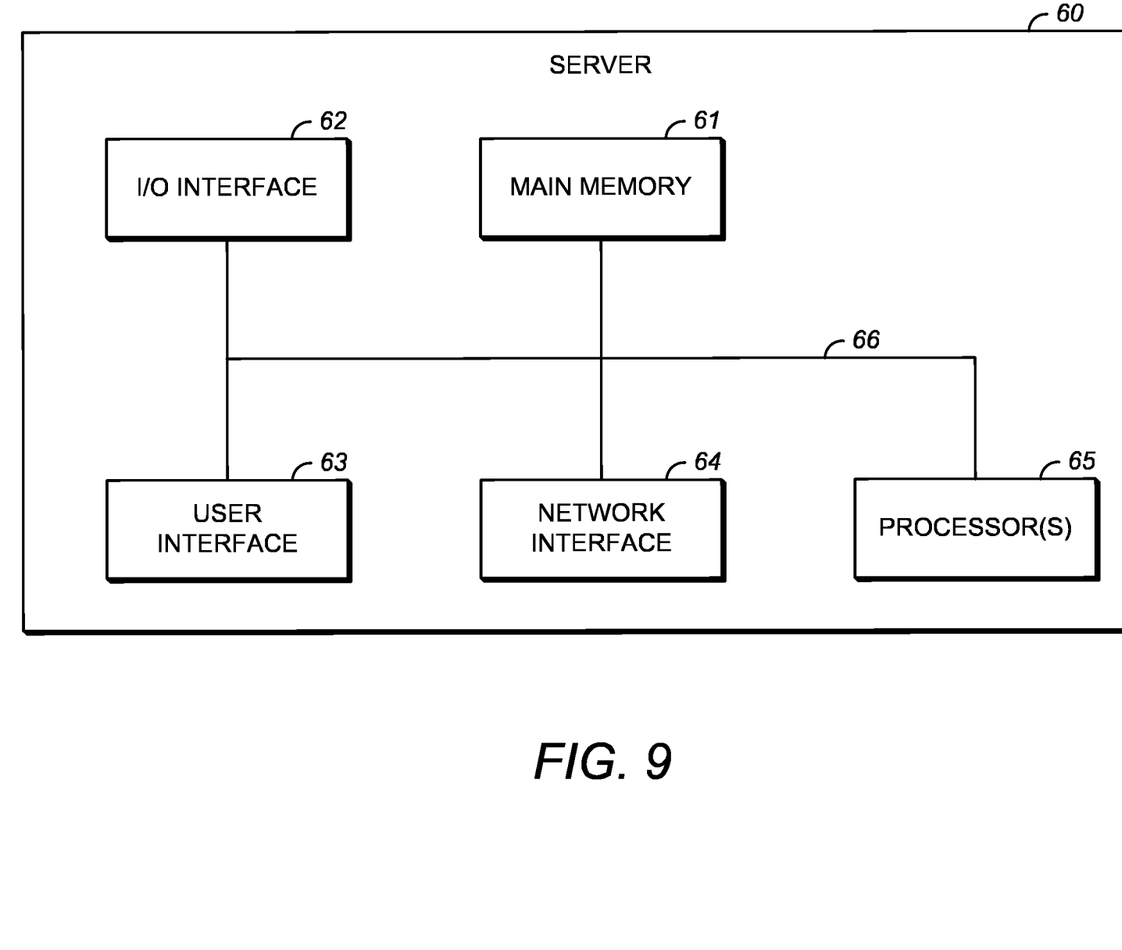
FIG. 9 is a schematic diagram of an exemplary server according to an embodiment of the present disclosure.

FIG. 9 is a schematic diagram of an exemplary system server according to an embodiment. It is contemplated by the present disclosure that the server 60 shown in FIG. 8 is representative of the server 4 shown in FIG. 1. It is also contemplated by the present disclosure that the server 60 includes electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium.

As shown in FIG. 9, the exemplary server 60 includes a main memory 61, an I/O interface 62, a user interface 63, a network interface 64, and one or more processors 65. The main memory 61 can be a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy.

The main memory 61 can be used to store any type of instructions associated with algorithms, processes, or operations for controlling the general functions of the server 60 as well as any operating system such as Linux, UNIX, Windows Server, or other customized and proprietary operating systems. The I/O interface 62 can be an interface for enabling the transfer of information between server 60 and external devices such as peripherals connected to the server 60 that need special communication links for interfacing with the one or more processors 65. The I/O interface 62 can be implemented to accommodate various connections to the server 60 that include, but is not limited to, a universal serial bus (USB) connection, parallel connection, a serial connection, coaxial connection, a wireless connection, a High-Definition Multimedia Interface (HDMI) connection SPI connection, other serial transport connection, or other known connection in the art for connecting to external devices.

The user interface 63 is implemented for allowing communication between a user and the server 60. The user interface 63 includes, but is not limited to, a mouse, a keyboard, a liquid crystal display (LCD), cathode ray tube (CRT), thin film transistor (TFT), light-emitting diode (LED), high definition (HD) or other similar display device with touch screen capabilities. Other kinds of input devices can be used to provide for interaction with a user as well. For example, feedback provided to the user can be any form of sensory feedback (e.g. visual feedback, auditory feedback by way of a speaker, or tactile feedback), and input from the user can be received in any form, including acoustic, speech, or tactile input. Input devices and a microphone can be coupled to and convey information via the internal bus 66 by way of an input device interface. A speaker can be coupled to and receive information via the internal bus 66 by way of a speaker interface. The exemplary server 60 can omit or one or more of the display, display interface, input device, microphone, speaker, input device interface, and speaker interface. The network interface 64 is a software and/or hardware interface implemented to establish a connection between the server 60, and other servers in the system as well as well as with the self-describing module 1, medical monitoring device 2, optional monitoring device mount 3, as described in FIG. 1. It is contemplated by the present disclosure that that network interface 64 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), and wireless local area networks (WLANs), system area networks (SANs), and other similar networks.

The one or more processors 65 are used for controlling the general operations of the server 60. Each one or the one or more processors 65 can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of the self-describing module 1, medical monitoring device 2, optional monitoring device mount 3. Communication between the components of the server 60 (e.g., 61-65) are established using an internal bus 66.

The present disclosure may be implemented as any combination of an apparatus, a system, an integrated circuit, and a computer program on a non-transitory computer readable recording medium. The one more processors may be implemented as an integrated circuit (IC), an application specific integrated circuit (ASIC), or large scale integrated circuit (LSI), system LSI, super LSI, or ultra LSI components which perform a part or all of the functions of the secure conditional access architecture.

The present disclosure includes the use of computer programs or algorithms. The programs or algorithms can be stored on a non-transitory computer-readable medium for causing a computer, such as the one or more processors, to execute the steps described in FIGS. 1-5. For example, the one or more memories stores software or algorithms with executable instructions and the one or more processors can execute a set of instructions of the software or algorithms in association with executing generating, processing provisioning requests and provisioning messages, as described in FIGS. 1-5.

The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices (PLDs), used to provide machine instructions or data to a programmable data processor, including a computer-readable recording medium that receives machine instructions as a computer-readable signal.

By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner.

The subject matter of the present disclosure is provided as examples of methods and programs for performing the features of the secure conditional access architecture. However, further features or variations are contemplated in addition to the features described above. It is contemplated that the implementation of the components and functions of the present disclosure can be done with any newly arising technology that may replace any of the above implemented technologies.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

We claim:

1. A method of using a self-describing module for updating data in a monitoring device mount, the method comprising:

transmitting a metadata block (MDB) from the self-describing module to the monitoring device mount using a communication interface, the MDB including at least identification (ID) data and configuration data;

associating the ID data from the MDB with ID data of a plurality of sub-systems of the monitoring device mount; and updating configuration data of at least one sub-system of the monitoring device mount with the configuration data in the MDB based on a result of the association between ID data from the MDB and the ID data of the plurality of sub-systems.

2. The method according to claim 1, wherein the monitoring device mount is connected to at least one sensor.

3. The method according to claim 1, further comprising storing the MDB in memory of the monitoring device mount as an instance of MDB data prior to associating the ID data from the MDB with ID data of the plurality of sub-systems of the monitoring device mount.

4. The method according to claim 1, wherein the monitoring device mount comprises one or more metadata plug-in interfaces (MPI) and the MDB of the self-describing module comprises a plurality of plug-ins that connect to the MPI.

5. The method according to claim 4, wherein each MPI is part of a sub-system of the plurality of sub-systems.

6. The method according to claim 4, wherein the ID data includes a namespace identifier for association with the MPI of the sub-system supporting a particular namespace.

7. The method according to claim 1, further comprising, prior to transmitting the MDB from the self-describing module to the monitoring device mount, establishing communication between the self-describing module and the monitoring device mount through the communication interface.

8. The method according to claim 1, further comprising detecting the self-describing module, connected through the communication interface to the monitoring device mount.

9. The method according to claim 1, further comprising identifying readiness of each sub-system to process data based on an announcement transmitted from each sub-system of the monitoring device mount.

10. The method according to claim 9, wherein the announcement is a ready signal transmitted to the self-describing module from the monitoring device mount once all sub-systems of the plurality of sub-systems are ready for transmission.

11. The method according to claim 4, further comprising placing the monitoring device mount into a service mode that is protected to enable uploads of new versions of the MDB and MPIs.

12. The method according to claim 3, wherein in response to the self-describing module being disconnected from the monitoring device mount, the instance of MDB data from the self-describing module is removed from the memory of the monitoring device mount and in response to the self-describing module being reconnected to the monitoring device mount, the method is repeated.

13. The method according to claim 12, wherein at least algorithms, features, and software are updated in the MDB of the self-describing module and reconnected to the monitoring device mount for the updated data from the MDB to be updated into at least one of the sub-systems of the monitoring device mount.

14. The method according to claim 1, wherein new parameters are added to the MDB and updated into the plurality of sub-systems of the monitoring device mount.

15. The method according to claim 1, wherein the MDB of the self-describing module includes a subset of a medical device communication standards to describe and communicate a state of the self-describing module.

16. The method according to claim 1, wherein the self-describing module is a patient monitoring module configured to acquire and process data generated by at least one physiological sensor configured to monitor a physiological parameter of a patient.

17. The method according to claim 16, further comprising transmitting updated sub-system modifications in the device from a user input to the self-describing module in reference to parameters of the physiological sensors monitoring a patient.

18. A non-transitory computer-readable recording medium in each of the self-describing module and monitoring device mount for updating data in the monitoring device mount, each non-transitory computer-readable recording medium storing one or more programs which when executed by a respective processor performs the method according to claim 1.

19. The method according to claim 1, wherein:
ID data of the MDB determined to be associated with an ID of a sub-system of the monitoring device mount causes the sub-system to be updated with the configuration data, and
ID data of the MDB determined not to be associated with any ID of the plurality of sub-systems of the monitoring device mount causes the ID data and its configuration data to be ignored by the monitoring device mount.

20. The method according to claim 1, wherein the ID data comprises a plurality of IDs, each ID having configuration data used to update a different sub-system of the plurality of sub-systems.

21. The method according to claim 1, wherein the configuration data includes at least one setting that configures a physiological algorithm according to a user changeable filter setting.

22. The method according to claim 21, wherein a user changeable filter setting is a setting adjusted according to an age demographic of a patient.

* * * * *